(12) United States Patent
Holguin et al.

(10) Patent No.: US 6,706,836 B1
(45) Date of Patent: Mar. 16, 2004

(54) HYDROPHILIC POLYMERS, PRESSURE SENSITIVE ADHESIVES AND COATINGS

(75) Inventors: Daniel L. Holguin, Fullerton, CA (US); H. Paul Barker, Sherman Oaks, CA (US); Ivan S. P. Lee, Arcadia, CA (US); Kenneth S. Lin, San Marino, CA (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 09/540,252

(22) Filed: Mar. 31, 2000

(51) Int. Cl.$^7$ ............................................. C08F 220/68

(52) U.S. Cl. ................... 526/320; 526/328.5; 526/319; 526/74; 526/89; 526/210; 526/212; 526/217; 526/317.1; 526/318.3; 526/318.4; 526/318.42; 526/329.2; 428/41.5

(58) Field of Search ........................... 526/74, 89, 210, 526/212, 217, 317.1, 318.3, 318.4, 318.42, 329.2, 320; 428/50

(56) References Cited

U.S. PATENT DOCUMENTS

| | | |
|---|---|---|
| 2,976,576 A | 3/1961 | Wichterle et al. |
| 3,220,960 A | 11/1965 | Wichterle et al. |
| 3,567,760 A | 3/1971 | Feldman et al. |
| 3,576,760 A | 4/1971 | Gould et al. |
| 3,813,695 A | 6/1974 | Podell, Jr. et al. |
| 3,963,685 A | 6/1976 | Abrahams |
| 4,275,138 A | 6/1981 | Kita et al. |
| 4,303,066 A | 12/1981 | D'Andrea |
| 4,356,288 A | 10/1982 | Lewis et al. |
| 4,379,863 A | 4/1983 | Snyder |
| 4,482,577 A | 11/1984 | Goldstein et al. |
| 4,499,154 A | 2/1985 | James et al. |
| 4,563,184 A | 1/1986 | Korol |
| 4,575,476 A | 3/1986 | Podell et al. |
| 4,593,053 A | 6/1986 | Jevne et al. |
| 4,732,786 A | 3/1988 | Patterson et al. |
| 4,768,523 A | 9/1988 | Cahalan et al. |
| 4,812,549 A | 3/1989 | Muramoto et al. |
| 4,892,787 A | 1/1990 | Kruse et al. |
| 4,935,307 A | 6/1990 | Iqbal et al. |
| 4,994,267 A * | 2/1991 | Sablotsky .................... 424/78 |
| 5,034,154 A | 7/1991 | Yezrielev et al. |
| 5,190,805 A | 3/1993 | Atherton et al. |
| 5,206,071 A | 4/1993 | Atherton et al. |
| 5,225,473 A | 7/1993 | Duan |
| 5,336,208 A | 8/1994 | Rosenbluth et al. |
| 5,478,631 A | 12/1995 | Kawano et al. |
| 5,508,366 A | 4/1996 | Andrist et al. |
| 5,516,865 A | 5/1996 | Urquiola |
| 5,580,565 A | 12/1996 | Tighe et al. |
| 5,601,723 A * | 2/1997 | Kirk et al. .................. 210/701 |
| 5,665,477 A | 9/1997 | Meathrel et al. |
| 5,672,392 A | 9/1997 | De Clercq et al. |
| 5,695,484 A | 12/1997 | Cox |
| 5,700,585 A | 12/1997 | Lee |
| 5,712,346 A | 1/1998 | Lee |
| 5,807,937 A * | 9/1998 | Matyjaszewski et al. ... 526/135 |

FOREIGN PATENT DOCUMENTS

| | | | |
|---|---|---|---|
| DE | 19516111 A1 | 11/1996 | |
| EP | 024164 A1 | 2/1981 | |
| EP | 0716929 A1 | 6/1996 | |
| JP | 2-22302 A | 1/1990 | |
| JP | 402022302 A * | 1/1990 | ............. C08F/2/22 |
| WO | WO 92/11825 | 7/1992 | |
| WO | WO 99/06454 | 2/1999 | |

OTHER PUBLICATIONS

Polymer International, vol. 36, No. 4, p. 303–308 (Apr. 1995).

Cuang, et al. "Avery Adhesive Test, AAT," Adhesive Age, vol. 40, No. 10, p. 18–23 (1997).

E.P. Chang, "Visoelastic Windows of Pressure–Senstive Adhesives," J. Adhesion, vol. 34, p. 189–200, (1991).

E. P. Chang, "Visoelastic Properties of Pressure–Sensitive Adhesives," J. Adhesion, p. 233–248, (1997).

* cited by examiner

Primary Examiner—Tatyana Zalukaeva
(74) Attorney, Agent, or Firm—Renner, Kenner, Greive, Bobak, Taylor & Weber (57) ABSTRACT

A method for the preparation of gel-free poly 2-hydroxyethyl methacrylate substantially in the absence of a chain transfer agent, comprising introducing monomeric 2-hydroxyethyl methacrylate containing ethylene glycol dimethacrylate impurities in the range of about 0.05 to 0.1% by weight into alcohol, polymerizing the 2-hydroxyethyl methacrylate to form a polymerization mixture, and removing the alcohol. Hydrophilic pressure sensitive adhesives are provided by adding polyethylene glycol to the polymerization mixture prior to removing the alcohol. A method for the preparation of an acrylic emulsion ink jet receptive clear coating, comprising forming a alkyl acrylate monomer-containing pre-emulsion feed mixture, introducing an activator into the alkyl acrylate monomer-containing pre-emulsion feed mixture, reacting a water soluble monomer feed in the alkyl acrylate monomer-containing pre-emulsion feed mixture, the water soluble monomer feed comprising 2-hydroxyethyl methacrylate and a cationic monomer to form a clear polymer in the reaction mixture. In another embodiment, the clear polymer in the butyl acrylate-containing pre-emulsion feed mixture is subsequently reacted with a water insoluble monomer feed mixture comprising 2-hydroxyethyl methacrylate, n-vinyl pyrrolidone, butyl acrylate, and methacrylic acid to form a second clear polymer in addition to the clear polymer in the alkyl acrylate monomer containing pre-emulsion feed mixture.

15 Claims, 2 Drawing Sheets

HYDROPHILIC POLYMERS, PRESSURE SENSITIVE ADHESIVES AND COATINGS

FIELD OF THE INVENTION

This invention is directed to the method of preparing hydrophilic poly 2-hydroxyethyl methacrylate polymers and copolymers and to their use as pressure sensitive adhesives, hydrogels, and coatings.

BACKGROUND OF THE INVENTION

The family of synthetic hydrogels includes polyacrylic acid, polyvinyl pyrrolidone, polyvinyl alcohol, polyacrylamide, poly hydroxybutyl acrylate, and poly 2-hydroxyethyl methacrylate. In this family of synthetic hydrogels, poly 2-hydroxyethyl methacrylate and poly hydroxybutyl acrylate are water insoluble polymers prepared from a water soluble monomer. The other polymers require crosslinking to form a hydrogel with water.

2-Hydroxyethyl methacrylate polymers are of interest because of their biocompatibility as evidenced by excellent performance in animal implant studies. The extensive use of 2-hydroxyethyl methacrylate polymers for contact lenses for the eyes illustrates the non irritating nature of the polymers.

Other than commercial use in contact lenses, 2-hydroxyethyl methacrylate polymers have had limited commercial success, used at low percentages only, because of the nature of the monomer. Industrial grade 2-hydroxyethyl methacrylate monomer contains a small amount of crosslinker impurity which can cause gel formation during solvent polymerization. The 2-hydroxyethyl methacrylate monomer is water soluble and the 2-hydroxyethyl methacrylate polymer is water insoluble which causes difficulty in emulsion polymerization employing a high portion of 2-hydroxyethyl methacrylate monomer. The preparation of 2-hydroxyethyl methacrylate polymer therefore generally requires the use of very pure and expensive monomer or a very extensive and expensive polymerization process.

Requirements of high quality inkjet coatings include clarity, water resistance, good ink absorption with quick drying, and low surface friction to enhance sheet feeding in inkjet printers. Typical inkjet coatings satisfy the requirements of water resistance, good ink absorption with quick drying, and low surface friction through the use of mixtures of polymers, or polymers with pigments, however, these mixtures are not clear.

U.S. Pat. No. 2,976,576 describes the use of poly 2-hydroxyethyl methacrylate resin for contact lenses and body implants.

U.S. Pat. No. 3,220,960 describes the use of poly 2-hydroxyethyl methacrylate resin for contact lenses and body implants.

U.S. Pat. No. 3,567,760 describes the preparation of 2-hydroxyethyl methacrylate copolymers in methanol that are water soluble salts for entrapping drugs, pesticides, flavoring agents, and fragrances.

U.S. Pat. No. 3,963,685 describes the preparation of methanol soluble poly 2-hydroxyethyl methacrylate for wound care dressings using high purity 2-hydroxyethyl methacrylate monomer having not over 0.035 weight percent of alkylene glycol dimethacrylate impurities.

EP 024164A1 describes the preparation of methanol soluble poly 2-hydroxyethyl methacrylate using high purity 2-hydroxyethyl methacrylate monomer.

Polymer International, vol. 36 no. 4, pp.303–308 (April 1995), describes the preparation of dimethylformamide soluble poly 2-hydroxyethyl methacrylate using a chain transfer agent to prevent gellation.

U.S. Pat. No. 4,303,066 describes the use of a plasticized poly 2-hydroxyethyl methacrylate resin prepared from high purity monomer as a non-tacky synthetic film for skin burns, with shortened forming time by adding water to the mixture.

U.S. Pat. No. 4,593,053 describes the use of a plasticized polyvinyl pyrrolidone as a hydrophilic medical type pressure sensitive adhesive for biomedical electrodes and transdermal devices.

WO 92/11825 describes the use of plasticized poly 2-hydroxyethyl methacrylate resin as a hydrophilic medical type pressure sensitive adhesive for a medical device.

U.S. Pat. No. 5,225,473 describes the use of a UV cured plasticized polyvinyl pyrrolidone as a hydrophilic medical type pressure sensitive adhesive for biomedical electrodes and transdermal devices.

U.S. Pat. No. 4,892,787 describes coated paper for inkjet printing containing pigment, an acrylic emulsion, and a water soluble polymer.

U.S. Pat. No. 5,206,071 describes acrylic graft copolymers and water soluble polymers.

U.S. Pat. No. 5,478,631 describes an inkjet recording sheet using a pigment and an amphoteric ion latex.

EP 0716929A1 describes acrylic graft copolymers and water soluble polymers.

DE 19516111A1 describes water soluble copolymers with crosslinkers.

U.S. Pat. No. 5,672,392 describes the preparation of recording materials for inkjet printers using acrylic emulsions and water soluble polymers.

The present invention is directed to providing a cost-effective method for the preparation of hydrophilic 2-hydroxyethyl methacrylate polymers and copolymers with utility as coatings and pressure sensitive adhesives.

The present invention is further directed to providing clear inkjet coatings without pigments that are water resistant and have good ink absorption with quick drying.

SUMMARY OF THE INVENTION

A method is provided for the preparation of gel-free poly 2-hydroxyethyl methacrylate substantially in the absence of a chain transfer agent, comprising introducing monomeric 2-hydroxyethyl methacrylate containing ethylene glycol dimethacrylate impurities in the range of no more than about 0.05–0.1% by weight of the monomer, into alcohol, polymerizing the 2-hydroxyethyl methacrylate to form a polymerization mixture, and optionally removing the alcohol. The alcohol is preferably selected from one of methanol and ethanol. Hydrophilic pressure sensitive adhesives are provided by adding polyethylene glycol to the polymerization mixture prior to removing the alcohol. Flexible hydrophilic coatings also are provided by adding glycerin to the polymerization mixture prior to removing the alcohol by drying.

In another embodiment, the monomeric 2-hydroxyethyl methacrylate contains alkylene glycol methacrylate impurities in the range of no more than about 3% by weight, wherein the alkylene glycol methacrylate impurities are selected from the group consisting of ethylene glycol dimethacrylate, diethylene glycol monomethacrylate, methacrylic acid and mixtures thereof.

A method is also provided for the preparation of a gel free, hydrophilic, water soluble polymer substantially in the absence of a chain transfer agent comprising a copolymer of 2-hydroxyethyl methacrylate and acrylic acid or methacrylic acid, including introducing monomeric 2-hydroxyethyl methacrylate into water solution with one of acrylic acid and methacrylic acid, adjusting the pH of the solution to a pH in the range of greater than about pH 3 to less than about pH 9, and copolymerizing the monomeric 2-hydroxyethyl methacrylate and acrylic or methacrylic acid.

In one embodiment, the monomeric 2-hydroxyethyl methacrylate contains at least 0.05% by weight, based on the monomer, of ethylene glycol dimethacrylate.

In another embodiment, hydrogels are prepared with copolymer concentrations greater than about 35% by weight.

In another embodiment, the copolymer of 2-hydroxyethyl methacrylate and acrylic acid or methacrylic acid is blended with a polyalkylene glycol, such as polyethylene glycol, to form a pressure sensitive adhesive.

In another embodiment, the copolymer of 2-hydroxyethyl methacrylate and acrylic acid or methacrylic acid is blended with glycerin to form a flexible coating.

A method is also provided for the preparation of a gel free hydrophilic polymer substantially in the absence of a chain transfer agent comprising a copolymer of 2-hydroxyethyl methacrylate and 4-hydroxybutyl acrylate, including introducing monomeric 2-hydroxyethyl methacrylate containing no more than about 0.05–0.1% by weight of ethylene glycol dimethacrylate into an alcohol solution with 4-hydroxybutyl acrylate, polymerizing the 2-hydroxyethyl methacrylate and 4-hydroxybutyl acrylate to form a polymerization mixture, and removing the alcohol. The alcohol is selected from one of methanol and ethanol, with ethanol being preferred.

In another embodiment, the monomeric 2-hydroxyethyl methacrylate contains no more than about 3% by weight alkylene glycol methacrylate impurities, wherein the alkylene glycol methacrylate impurities are selected from the group consisting of ethylene glycol dimethacrylate, diethylene glycol monomethacrylate, methacrylic acid and mixtures thereof.

A method of preparing an acrylic emulsion ink jet receptive clear coating is also provided comprising: forming an alkyl acrylate monomer-containing pre-emulsion feed mixture, introducing an activator into the alkyl acrylate monomer-containing pre-emulsion feed mixture, reacting a water soluble monomer feed in said alkyl acrylate monomer-containing pre-emulsion feed mixture, said water soluble monomer feed comprising 2-hydroxyethyl methacrylate and n-vinylpyrrolidone, to form a clear polymer in said alkyl acrylate monomer-containing pre-emulsion feed mixture.

In another embodiment, the method further comprises subsequently reacting with said clear polymer in said alkyl acrylate monomer-containing pre-emulsion feed mixture, a water insoluble monomer feed mixture comprising 2-hydroxyethyl methacrylate, n-vinyl pyrrolidone, butyl acrylate, and methacrylic acid to form a clear polymer over said polymer in said alkyl acrylate monomer-containing pre-emulsion feed mixture.

A method for the preparation of a powdered low gel poly 2-hydroxyethyl methacrylate substantially in the absence of a chain transfer agent is also provided comprising: introducing monomeric 2-hydroxyethyl methacrylate containing ethylene glycol dimethacrylate impurities in the range of no more than about 0.05 to about 0.1% by weight, based on the monomer, into water, polymerizing the 2-hydroxyethyl methacrylate, drying said polymerized the 2-hydroxyethyl methacrylate, and grinding said dried polymerized 2-hydroxyethyl methacrylate to form a powder.

In another embodiment, the monomeric 2-hydroxyethyl methacrylate contains no more than about 3% by weight alkylene glycol methacrylate impurities, wherein the alkylene glycol methacrylate impurities are selected from the group consisting of ethylene glycol dimethacrylate, diethylene glycol monomethacrylate, methacrylic acid and mixtures thereof.

In another embodiment, said poly 2-hydroxyethyl methacrylate powder is blended with a polyalkylene glycol, such as polyethylene glycol to form a pressure sensitive adhesive.

The term "low gel" as used in the specification refers to a poly 2-hydroxyethyl methacrylate (polyHEMA) polymer having less than 15% gel content, as determined by the method described hereinbelow.

The term "gel free" as used in the specification refers to a polyHEMA polymer having less than 5% gel content, as determined by visual inspection or by the "gel content" method described hereinbelow. The presence of any gel in the polymeric product was determined by pouring a thin film of the product and visually inspecting for any particulate.

The "gel content" of the poly HEMA polymers is a measure of the polymer that is insoluble in methanol (MeOH). The gel content is determined as follows: The poly HEMA adhesive polymer is coated onto a silicone release liner and dried at 70° C. for 15 minutes. The adhesive is removed from the release liner, and a 60 to 80 mg sample of the adhesive is accurately weighed out and placed into a 10 μm PTFE membrane filter. The edges of the filter are thermally sealed to contain the sample, and the filter is placed in a vial containing about 15 g of methanol. The vial is agitated for 72 hours, and the filter is taken out of the solvent and dried at 120° C. for 120 minutes.

The filter is then weighed, and the resulting weight of the sample is used to calculate the percent gel as follows:

$$\% \text{ gel} = (b/a) \times 100$$

wherein, a=initial weight of the sample, and b=final weight of the sample.

DETAILED DESCRIPTION OF THE INVENTION

In one embodiment, the present invention provides a method for the preparation of a gel-free poly 2-hydroxyethyl methacrylate substantially in the absence of a chain transfer agent. The method includes introducing monomeric 2-hydroxyethyl methacrylate containing ethylene glycol dimethacrylate impurities in the range of no more than about 0.05 to 0.1% by weight into an alcohol selected from one of methanol and ethanol, polymerizing the 2-hydroxyethyl methacrylate to form a polymerization mixture, and removing the alcohol. Polymerizing is induced by free radical initiation, and the alcohol is preferably removed by coating a substrate and drying the mixture. In one embodiment, the monomeric 2-hydroxyethyl methacrylate contains alkylene glycol impurities in a total amount of no more than 3% by weight, and the impurities are selected from the group consisting of ethylene glycol dimethacrylate, diethylene glycol monomethacrylate, methacrylic acid and mixtures thereof. The controlled level of impurities results in the gel free polymer, even without using ultra-pure monomer.

As described above, free radical polymerization is initiated by a suitable initiator. The initiator must be soluble in the alcohol and the 2-hydroxyethyl methacrylate monomer mixture. Suitable initiators that are soluble in alcohol include, but are not limited to, peroxides such as benzoyl peroxide, and azo compounds, such as 2,2'-azobis (isobutyronitrile).

The method of the present invention, therefore, provides for the cost effective preparation of a gel-free poly 2-hydroxyethyl methacrylate, substantially in the absence of a chain transfer agent, using industrial grade 2-hydroxyethyl methacrylate monomer. A 2-Hydroxyethyl methacrylate monomer suitable for use in the method of the present invention is available from Mitsubishi Rayon, Japan.

In another embodiment, the present invention provides a method for the preparation of a gel-free poly 2-hydroxyethyl methacrylate substantially in the absence of a chain transfer agent, to achieve a hydrophilic pressure sensitive adhesive. The method includes introducing monomeric 2-hydroxyethyl methacrylate containing ethylene glycol dimethacrylate impurities in the range of about 0.05 to 0.1% by weight into an alcohol selected from one of methanol or ethanol, polymerizing the 2-hydroxyethyl methacrylate to form a polymerization mixture, adding a polyalkylene glycol, such as polyethylene glycol in a range of about 40% to about 70% by weight, based on the weight of the polymer and the polyethylene glycol, and removing the alcohol to form a hydrophilic pressure sensitive adhesive. Polymerization is induced by free radical initiation, and alcohol removal is preferably accomplished by coating the mixture onto a substrate and drying the mixture. Although the preferred polyalkylene glycol used to prepare the pressure sensitive is polyethylene glycol, other polyalkylene glycols, such as polypropylene glycol may be used. In addition, copolymers of ethylene and propylene glycol may also be used to form the pressure sensitive adhesive.

In another embodiment, the 2-hydroxyethyl methacrylate contains alkylene glycol impurities in a total amount of no more than about 3% by weight of monomer, and the impurities are selected from the group consisting of ethylene glycol dimethacrylate, diethylene glycol monomethacrylate, methacrylic acid and mixtures thereof. The hydrophilic pressure sensitive adhesives formed by this method have utility in many label and tape applications, and is particularly suitable for medical applications.

In yet another embodiment, the present invention provides a method for the preparation of a flexible hydrophilic coating comprising a gel-free poly 2-hydroxyethyl methacrylate produced substantially in the absence of a chain transfer agent. The method comprises introducing monomeric 2-hydroxyethyl methacrylate containing ethylene glycol dimethacrylate impurities in the range of about 0.05 to 0.1% by weight into an alcohol selected from one of methanol and ethanol, polymerizing the 2-hydroxyethyl methacrylate to form a polymerization mixture, adding glycerin to the polymerization mixture in an amount from about 10% to about 50% by weight of the polymer, preferably about 25% by weight of the polymer, and removing the alcohol to form a flexible hydrophilic coating. Polymerization is induced by free radical initiation, and alcohol removal by coating the mixture and drying.

In another embodiment, the 2-hydroxyethyl methacrylate contains alkylene glycol methacrylate impurities in the range of about 3%, based on the weight of the monomer. Preferably, the alkylene glycol impurities are selected from the group consisting of ethylene glycol dimethacrylate, diethylene glycol monomethacrylate, methacrylic acid and mixtures thereof, in a total amount of no more than about 3% by weight of monomer. The flexible hydrophilic coating formed by this method has utility in skin-friendly applications in which a high Moisture Vapor Transmission Rate (MVTR) is needed together with protective, skin barrier properties. The coating is also suitable for printable coatings, such as inkjet coatings for paper, plastic film, and the like.

While the above methods involve the formulation of a homopolymer of the 2-hydroxethyl methacrylate monomer, the present invention also provides a method for the preparation of a gel free, hydrophilic, water soluble polymer comprising a copolymer of 2-hydroxyethyl methacrylate and acrylic acid or methacrylic acid. This method includes introducing monomeric 2-hydroxyethyl methacrylate into water solution with one of acrylic acid and methacrylic acid in weight ratio in the range of about 3 to about 15%, adjusting the pH of the solution to a pH in the range of greater than about pH 3 to less than about pH 9, and copolymerizing the monomeric 2-hydroxyethyl methacrylate and acrylic or methacrylic acid. Copolymerization is induced by free radical initiation. A pH of 3 or less and a pH of 9 or greater should be avoided, because the reactants may precipitate out or not form a useable copolymer.

In one preferred embodiment, the method of forming a copolymer of 2-hydroxyethyl methacrylate and one of acrylic acid and methacrylic acid includes introducing monomeric 2-hydroxyethyl methacrylate into water solution with one of acrylic acid and methacrylic acid in weight ratio in the range of about 3 to about 15%, adjusting the pH of the solution to at least pH 5, and copolymerizing the monomeric 2-hydroxyethyl methacrylate and acrylic or methacrylic acid.

In one embodiment, the 2-hydroxyethyl methacrylate monomer contains at least 0.05% by weight of ethylene glycol dimethacrylate.

An initiator is added to the mixture of the monomeric 2-hydroxyethyl methacrylate and acrylic or methacrylic acid in an amount effective to initiate copolymerization. Suitable initiators include dissociative initiators and redox initiators. Suitable dissociative initiators that may be used in the present invention include, but are not limited to, persulfates such as ammonium persulfate, potassium persulfate and sodium persulfate, hydrogen peroxide, tert-butyl hydroperoxide, and azo compounds such as 4,4'-azobis(4-cyanovaleric acid). Redox initiators include, but are not limited to, persulfates with bisulfate, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

In a preferred embodiment, methacrylic acid is used. In another preferred embodiment, the hydrophilic copolymer comprises from about 90% to about 95% by weight 2-hydroxyethyl methacrylate.

In the preparation of the hydrophilic copolymer of 2-hydroxyethyl methacrylate and methacrylic acid or acrylic acid of the present invention, it is preferable to raise the pH of the monomer mixture to at least a pH of about 5 in order to neutralize the monomer mixture before polymerization to prevent the precipitation of the polymer as it is formed. The pH adjustment may be accomplished by adding aqueous ammonium hydroxide or other basic chemical(s) known to those skilled in the art. The hydrophilic copolymer that is formed is soluble in methanol and soluble in water at concentrations up to about 35% by weight. At concentrations greater than about 35% by weight in water, the hydrophilic copolymer becomes a hydrogel.

By definition, a hydrogel is swellable with water and insoluble in water, forms an equilibrium state with water, and maintains its equilibrium shape. The hydrophilic copolymers of 2-hydroxyethyl methacrylate and methacrylic acid or acrylic acid of this invention meet all of the criteria for a hydrogel at polymer concentrations greater -than about 35% by weight without the necessity of crosslinking. Hydrogels at lower concentrations of polymer can meet this criteria with crosslinking with formaldehydes, metal salts, aziridines, isocyanates, dichromates, and the like, in the amount of up to about 10% by weight of polymer. If the copolymers are crosslinked, then the amount of crosslinker is preferably less than about 10% by weight of the polymer if crosslinkers other than isocyanates are used, and up to about 20% by weight of the polymer if isocyanates are used.

In another embodiment, the present invention provides a method for the preparation of substantially gel-free, hydrophilic, water soluble copolymers of 2-hydroxyethyl methacrylate and methacrylic acid or acrylic acid substantially in the absence of a chain transfer agent, to achieve a hydrophilic pressure sensitive adhesive. The method includes introducing monomeric 2-hydroxyethyl methacrylate into water solution with one of acrylic acid and methacrylic acid, adjusting the pH of the monomer mixture to a pH in the range of greater than about pH 3 to about less than pH 9, copolymerizing the 2-hydroxyethyl methacrylate and acrylic or methacrylic acid to form a polymerization mixture, adding a polyalkylene glycol, such as polyethylene glycol in a range of about 40% to about 70% by weight, based on the weight of the polymer and the polyethylene glycol, to the polymerization mixture, and removing the water to form a hydrophilic pressure sensitive adhesive. Polymerization is induced by free radical initiation, and water removal is preferably accomplished by coating the mixture onto a substrate and drying the mixture. Although the preferred polyalkylene glycol used to prepare the pressure sensitive is polyethylene glycol, other polyalkylene glycols, such as polypropylene glycol may be used. In addition, copolymers of ethylene and propylene glycol may also be used to form the pressure sensitive adhesive.

In one preferred embodiment, the method of forming a copolymer of 2-hydroxyethyl methacrylate and one of acrylic acid and methacrylic acid includes introducing monomeric 2-hydroxyethyl methacrylate into water solution with one of acrylic acid and methacrylic acid in weight ratio in the range of about 3 to about 15%, adjusting the pH of the solution to at least pH 5, and copolymerizing the monomeric 2-hydroxyethyl methacrylate and acrylic or methacrylic acid.

In yet another embodiment, the present invention provides a method for the preparation of a flexible hydrophilic coating comprising a substantially gel-free hydrophilic copolymer of 2-hydroxyethyl methacrylate and methacrylic acid and acrylic acid produced substantially in the absence of a chain transfer agent. The method comprises introducing monomeric 2-hydroxyethyl methacrylate into water solution with one of acrylic acid and methacrylic acid, adjusting the pH of the monomer mixture to a pH in the range of greater than about pH 3 to about less than pH 9, copolymerizing the 2-hydroxyethyl methacrylate and acrylic or methacrylic acid to form a polymerization mixture, adding glycerin to the polymerization mixture in an amount from about 10% to about 50% by weight of the polymer, preferably about 25% by weight of the polymer, and removing the water to form a flexible hydrophilic coating, which is particularly suited for medical and skin care. Polymerization is induced by free radical initiation, and water removal by coating the mixture and drying.

In one preferred embodiment, the method of forming a copolymer of 2-hydroxyethyl methacrylate and one of acrylic acid and methacrylic acid includes introducing monomeric 2-hydroxyethyl methacrylate into water solution with one of acrylic acid and methacrylic acid in weight ratio in the range of about 3 to about 15%, adjusting the pH of the solution to at least pH 5, and copolymerizing the monomeric 2-hydroxyethyl methacrylate and acrylic or methacrylic acid.

In addition to the uses as hydrogels, pressure sensitive adhesives, and flexible films or coatings, the poly 2-hydroxyethyl methacrylate/acrylic acid or methacrylic acid copolymer prepared in water can also be used as an abrasion resistant coating for glass bottles. Crosslinkers and surfactants may be added to the poly 2-hydroxyethyl methacrylate/acrylic acid or methacrylic acid copolymer coatings to achieve optimum coating performance.

The crosslinker may be added to the copolymer in an amount from about 1 to about 10 percent by weight based on the weight of the copolymer. Suitable crosslinkers include, but are not limited to, formaldehydes, metal salts, aziridines, isocyanates, dichromates and the like. A preferred crosslinker that may be added to the copolymer is ammonium dichromate, and is added to the copolymer at about 7.5% by weight, based on the weight of the copolymer.

The surfactant may be added to the copolymer in an amount from about 0 to about 5 percent by weight based on the weight of the copolymer. Suitable surfactants include, but are not limited to, water dispersible silicone and fluorocarbon surfactants. A preferred surfactant that may be added to the copolymer is a silicone surfactant that is commercially available from Dow Corning, and is added to the copolymer at about 2% by weight, based on the weight of the copolymer.

The copolymer coating can be easily removed from the glass bottles by alkali treatment, such as an alkaline solution of 1% sodium hydroxide.

In another embodiment, the present invention provides a method for the preparation of a gel free hydrophilic polymer substantially in the absence of a chain transfer agent comprising a copolymer of 2-hydroxyethyl methacrylate and 4-hydroxybutyl acrylate, including introducing monomeric 2-hydroxyethyl methacrylate containing 0.05 to 0.1% by weight of ethylene glycol dimethacrylate impurities, into an alcohol solution with 4-hydroxybutyl acrylate, polymerizing the 2-hydroxyethyl methacrylate and 4-hydroxybutyl acrylate to form a polymerization mixture, and removing the alcohol. The alcohol is selected from one of methanol and ethanol, with ethanol being preferred.

In another embodiment, the monomeric 2-hydroxyethyl methacrylate contains no more than about 3% by weight of alkylene glycol methacrylate impurities.

The copolymer of 2-hydroxyethyl methacrylate and 4-hydroxybutyl acrylate is a hydrophilic copolymer that is insoluble in water and does not require crosslinking for water resistance. In addition, the copolymer of 2-hydroxyethyl methacrylate and 4-hydroxybutyl acrylate is flexible enough to form a flexible coating or film for medical and skin care or skin protection applications without the need for the addition of glycerin. The coating is also suitable for printable coatings, such as inkjet coatings for paper, plastic film, and the like. The flexible coating comprising the copolymer of 2-hydroxyethyl methacrylate and 4-hydroxybutyl acrylate is also useful as a Rubber or latex glove coating, with particular usefulness in wet-donning applications. Rubber or latex gloves require the ability of donning, that is, the ability to slide on and off the surface of the skin with minimal friction. The copolymer of 2-hydroxyethyl methacrylate and 4-hydroxybutyl acrylate provides a flexible, non-tacky glove coating that allows the donning, wet or dry, of the Rubber or latex glove with minimal blocking and without undue friction or clinging.

In addition to its applicability to hydrophilic coatings and pressure sensitive adhesives, the present invention provides a method for the preparation of an acrylic emulsion ink jet receptive clear coating. In this embodiment, the method includes forming an alkyl acrylate monomer-containing pre-emulsion feed mixture, introducing an activator into the alkyl acrylate monomer-containing pre-emulsion feed mixture, reacting a water soluble monomer feed in the alkyl acrylate monomer-containing pre-emulsion feed mixture, wherein the weight ratio of the alkyl acrylate monomer-containing pre-emulsion feed mixture to the water soluble monomer feed is from about 1:1 to about 1:2, to form a clear, transparent polymer in the alkyl acrylate monomer-containing emulsion feed mixture. The alkyl acrylate monomers may include, but are not limited to, ethyl acrylate, 2-ethylhexyl acrylate, butyl acrylate, isooctyl acrylate, and the like. A preferred alkyl acrylate monomer is butyl acrylate. The water soluble monomer feed comprises 2-hydroxyethyl methacrylate and a cationic monomer, such as n-vinylpyrrolidone, wherein the weight ratio range of the 2-hydroxyethyl methacrylate to the cationic monomer is from about 1:0 to about 1:1. The term "clear" as used herein to describe the polymer refers to a polymer product that does not include particulate or inclusions that would indicate incompatibilities in the polymerization process. The term "transparent" as used herein to describe the polymer refers to a polymer product that is capable of being seen through. Both "clear" and "transparent" appearances are based upon unaided, visual inspection.

In one embodiment, the 2-hydroxyethyl methacrylate contains at least 0.05% by weight of ethylene glycol dimethacrylate.

The acrylic emulsion ink jet receptive clear coating of the present invention does not require the addition of fillers or particulate to obtain ink absorbency, and is particularly useful with ink jet printers that use dye based inks.

In a variation of this embodiment, the preformed clear polymer in the alkyl acrylate monomer-containing emulsion mixture is subsequently reacted with a water insoluble monomer feed mixture, for example comprising 2-hydroxyethyl methacrylate, n-vinyl pyrrolidone, butyl acrylate, and methacrylic acid, in a weight ratio of about 20% to about 80% to form a second clear polymer substantially over the preformed clear polymer in the alkyl acrylate monomer-containing emulsion mixture.

The addition of the water soluble monomer feed to the alkyl acrylate monomer-containing pre-emulsion feed mixture produces a first clear, or core polymer formed in the alkyl acrylate monomer-containing pre-emulsion mixture. A second clear polymer, may be formed in the presence of the first polymer from a second monomer charge which is, in one embodiment, the water insoluble monomer feed comprising 2-hydroxyethyl methacrylate, n-vinyl pyrrolidone, butyl acrylate and methacrylic acid. The second clear polymer is formed substantially over the first clear polymer.

This polymerization process is known as sequential polymerization. It is believed that the product is a domain-type emulsion polymer in which the first or core particles form one domain and the second or shell copolymer forms a second domain which partially or continuously surrounds the core. By reserving a significant amount of the monomers to the second charge one can effectively use the monomers of the second charge to control properties.

Figure 1:
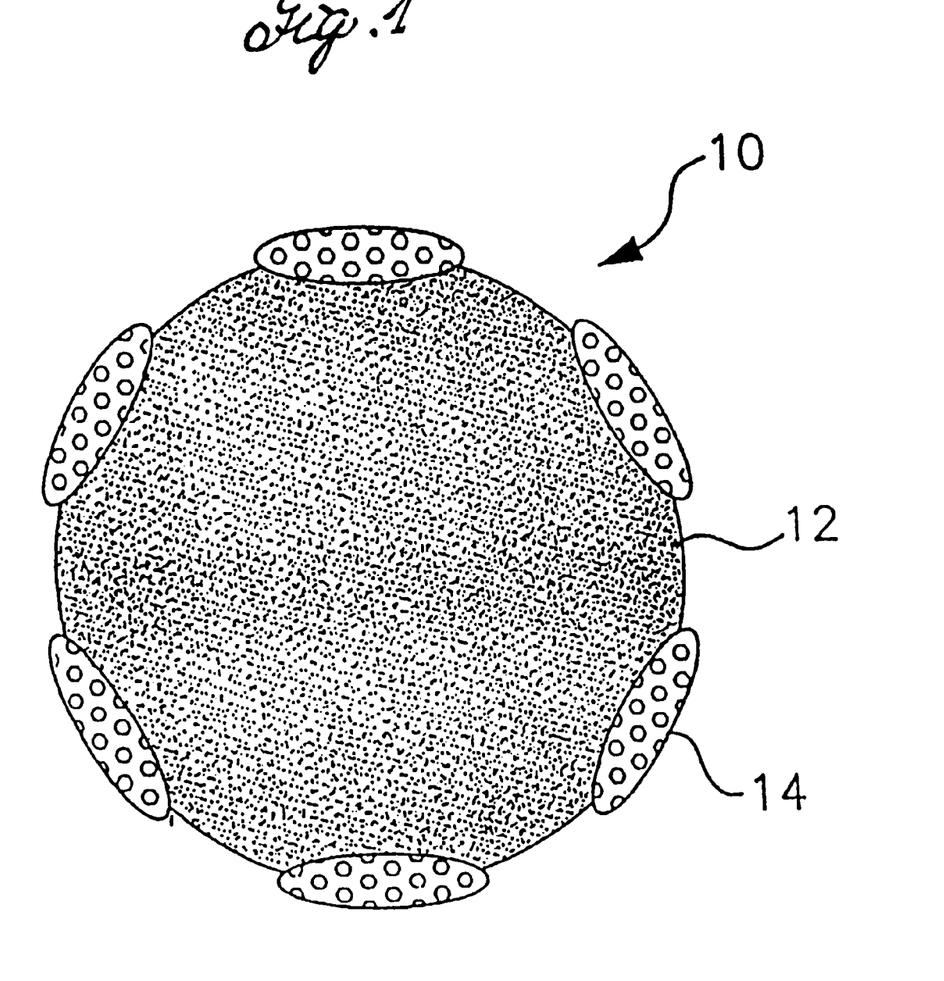
Figure 2:
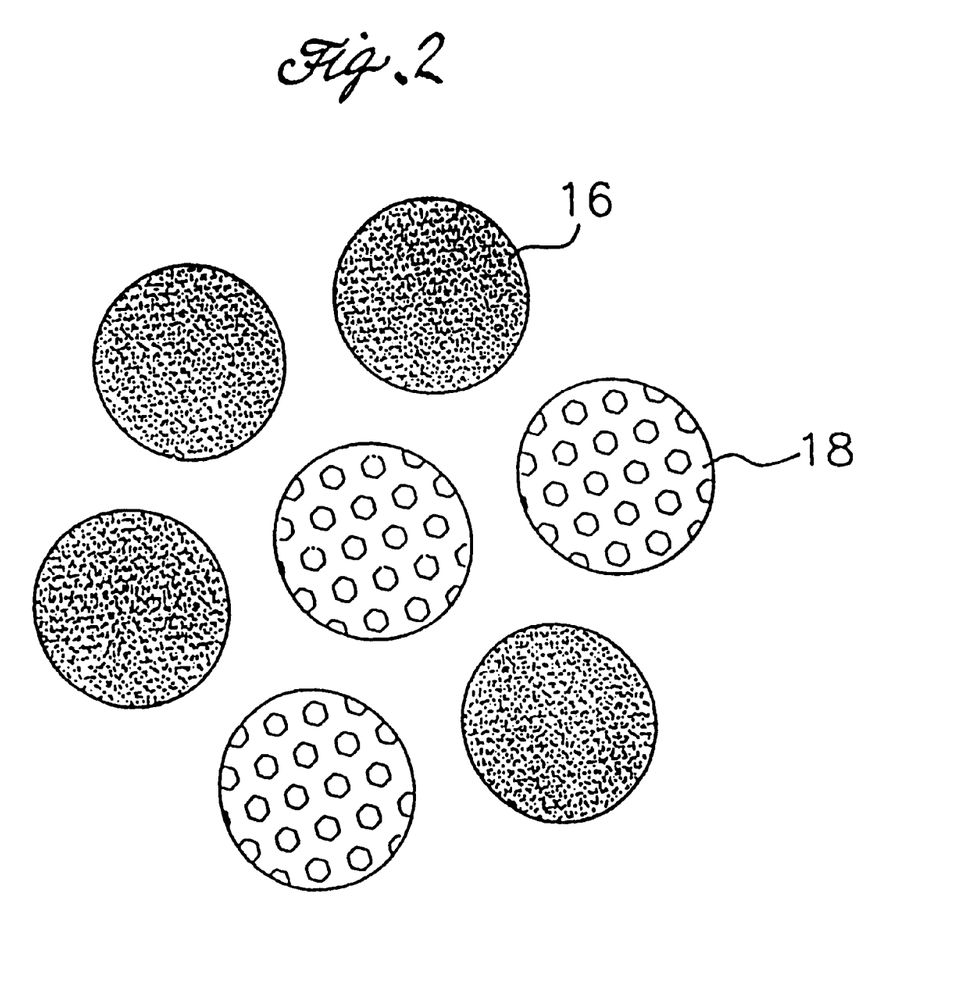

The two systems are depicted to FIGS. 1 and 2. With reference to FIG. 1, a sequentially polymerized polymer particle is formed in a reaction emulsion mixture as particle 10 and comprised of a central domain 12 completely or partially surrounded by a second stage polymerized outer domain 14. In their formation, the monomers of the inner domain are polymerized first, followed by polymerization of the monomers forming the outer domain which associate with and are believed to attach to the initially formed inner domain copolymer particles.

As depicted in FIG. 2, if the individual polymers are separately polymerized and mixed, they form a random blend of core 16 and shell 18 polymer particles with little or no attachment or association with each other.

As discussed above, an initiator is added to the monomeric 2-hydroxyethyl methacrylate monomers and, optionally, n-vinyl pyrrolidone, in an amount effective to initiate copolymerization. Suitable initiators include dissociative initiators and redox initiators. Suitable dissociative initiators include, but are not limited to, persulfates such as ammonium persulfate, potassium persulfate and sodium persulfate, hydrogen peroxide, tert-butyl hydroperoxide, and azo compounds such as 4,4'-azobis(4-cyanovaleric acid). Redox initiators include, but are not limited to, persulfates with bisulfate ion, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

A preferred activator is sodium formaldehyde sulfoxylate, preferably in an amount of about 0.1 to about 1 weight percent based on the weight of the polymer. The water insoluble monomer feed may further comprise an effective amount of an initiator, such as tert-butyl hydroperoxide or the like, and at least one water insoluble acrylate or methacrylate selected from methyl acrylate, methyl methacrylate, 2-ethylhexyl acrylate, butyl acrylate, trifluoroethyl methacrylate, and mixtures thereof in the amount of about 15 to about 35% by weight of the polymer, preferably from about 15% by weight of the polymer. Trifluoroethyl methacrylate is preferably included in the water insoluble monomer feed in an amount of about 1.5% by weight, based on the weight of the polymer. Inclusion of trifluoroethyl methacrylate results in the improvement of sheet feeding performance during inkjet printing.

The substrate which is used in the present invention may be any substrate material such as paper and polymeric films in the form of sheets and strips, and the like. Preferred types of paper include semi-gloss paper and high gloss paper. In one embodiment, the substrate is a polymeric film. In a preferred embodiment, the substrate is a polymeric film formed from a thermoplastic material. In a more preferred embodiment, the substrate is a polymeric film selected from the group consisting of polystyrene, a polyester, and a polyolefin such as polyethylene or polypropylene.

The acrylic emulsion ink jet receptive clear coatings of the present invention are particularly suited as coatings for clear films and high gloss photo quality paper. It is an advantage of the present invention that these acrylic emulsion ink jet receptive coatings are clear, water resistant, have good ink absorption with quick drying, and low surface friction to enhance sheet feeding in ink jet printers. It is also an advantage of the present invention that the above properties may be achieved without the use of pigments or mixtures of polymers that would be expected to reduce the clarity of the coatings.

In another embodiment, the present invention provides a method for the preparation of a powdered low-gel poly 2-hydroxyethyl methacrylate substantially in the absence of a chain transfer agent is also provided comprising: introducing monomeric 2-hydroxyethyl methacrylate containing ethylene glycol dimethacrylate impurities in the range of 0.05 to 0.1% by weight into water, polymerizing the 2-hydroxyethyl methacrylate, drying said polymerized 2-hydroxyethyl methacrylate, and grinding said dried polymerized 2-hydroxyethyl methacrylate to form a powder.

In another embodiment, the monomeric 2-hydroxyethyl methacrylate contains alkylene glycol methacrylate impurities in the range of no more than 3% by weight.

In a variation of this embodiment, the method for the preparation of a low-gel poly 2-hydroxyethyl methacrylate substantially in the absence of a chain transfer agent, comprises introducing monomeric 2-hydroxyethyl methacrylate containing ethylene glycol dimethacrylate impurities in the range of no more than about 0.05 to 0.1% by weight into water, polymerizing the 2-hydroxyethyl methacrylate to form a polymerization mixture, drying the polymerized 2-hydroxyethyl methacrylate, and grinding the dried polymerized 2-hydroxyethyl methacrylate to form a powder. The dry poly 2-hydroxyethyl methacrylate powder is then blended with a polyalkylene glycol, such as polyethylene glycol, to form a pressure sensitive adhesive, wherein the amount of the polyalkylene glycol used to prepare the pressure sensitive adhesive is from about 40 to about 70% by weight, based on the weight of the dry poly 2-hydroxyethyl methacrylate powder and the polyethylene glycol.

In another embodiment, the 2-hydroxyethyl methacrylate monomer contains alkylene glycol impurities that are selected from the group consisting of ethylene glycol dimethacrylate, diethylene glycol monomethacrylate, methacrylic acid and mixtures thereof, in a total amount of no more than about 3% by weight of monomer.

The hydrophilic pressure sensitive adhesive formed by this method has utility in many label and tape applications, and is particularly suitable for thick medical applications, and as an additive for cosmetic and skin care products. In another variation of this embodiment, the dry poly 2-hydroxyethyl methacrylate powder can be dissolved in alcohol and glycerin can be added to the polymerization mixture in an amount from about 10% to about 50% by weight of the polymer, preferably about 25% by weight of the polymer, and the alcohol removed to form a flexible hydrophilic coating. Before, the alcohol is removed, the solution can be sprayed onto the skin prior to applying a bandage, glove, or the like.

2-Hydroxyethyl methacrylate monomer suitable for use in the method of the present invention may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

The polymers and copolymers of the present invention may be applied to various substrates as described below by any conventional means known in the art such as die coating, roll coating, reverse roll coating, gravure coating, reverse gravure coating, offset gravure coating, Mayer rod or wire wound rod coating, spraying, brushing, and the like. The polymers and copolymers of the present invention may be heated or cooled to facilitate the coating process and to alter the depth or penetration into the substrate.

The amount of the polymers and copolymers of the present invention applied to a substrate may be varied depending upon the characteristics of the substrate, the characteristics desired to be imparted to the substrate, and the particular characteristics of the polymers and copolymers. For economic reasons, it is normally desired to apply the lowest amount of coating to obtain the desired result. Typically, the applied coating weights may, depending on the substrate and intended use, range from about 0.1 to about 100 grams/meter$^2$. For pressure sensitive adhesive applications, the amount is preferably in the range of about 15 grams/meter$^2$ to about 45 grams/meter$^2$. For hydrophilic coating and ink jet coating applications, the amount is preferably from about 1 gram/meter$^2$ to about 25 grams/meter$^2$.

Composites of the present invention may be prepared in various forms including webs which may be in roll form and which can thereafter be cut or slit into strips or sheets of desired dimensions.

The following examples illustrate the method of preparation of the hydrophilic polymers and copolymers of the present invention. In the following examples, Disponil FES-77 is alkylpolyglycol ether sulfate, sodium salt, available from Henkel Corp., of Ambler, Pa. Airvol 523 is polyvinyl alcohol, available from Air Products and Chemicals, Inc., of Allentown, Pa.

EXAMPLE 1

Preparation of poly 2-Hydroxyethyl Methacrylate in Ethanol

Recipe (1807 Gram Batch)

| Reactor Charge | |
|---|---|
| 2-Hydroxyethyl Methacrylate (Mitsubishi) | 540 grams |
| Ethanol | 1080 grams |
| Benzoyl peroxide | 2.7 grams |
| Cook-Off initiator #1 | |
| Ethanol | 60 grams |
| 2,2'-azobis(2,4-dimethylpentanenitrile)* | 1.4 grams |
| Cook-Off initiator #2 | |
| Ethanol | 60 grams |
| 2,2'-azobis(2,4-dimethylpentanenitrile)* | 1.4 grams |
| Cook-Off initiator #3 | |
| Ethanol | 60 grams |
| 2,2'-azobis(2,4-dimethylpentanenitrile)* | 1.4 grams |

*VAZO ®52 (2,2'-azobis(2,4-dimethylpentanenitrile) (Dupont; Wilmington, Delaware)

Procedure

1. The Reactor Charge was weighed out into a flask and poured into a reaction kettle with mixing, and was heated with an 80° C. jacket and a $N_2$ purge kettle.
2. The Cook-Off initiator #1 (Ethanol and VAZO®52) was weighed into a small beaker and mixed until the solids dissolved.
3. Three and one-half hours after the addition of the Reactor Charge, Cook-Off initiator #1 was added to the kettle.
4. The Cook-Off initiator #2 (Ethanol and VAZO®52) was weighed into a small beaker and mixed until the solids dissolved.
5. One hour after the addition of Cook-Off initiator #1, Cook-Off initiator #2 was added to the kettle.

6. The Cook-Off initiator #3 (Ethanol and VAZO®52) was weighed into a small beaker and mixed until the solids dissolved.
7. One hour after the addition of Cook-Off initiator #2, Cook-Off initiator #3 was added to the kettle.
8. One hour after the addition of Cook-Off initiator #3, the kettle contents were cooled and discharged.

The polymeric product synthesized in Example No. 1, above, exhibited the following properties:
   Appearance: clear to light-yellow gel-free liquid
   Solids: 30.5%
   Viscosity: 8,700 cPs
   Residual monomer: HEMA, 0.95%

2-hydroxyethyl methacrylates prepared with 2-hydroxyethyl methacrylate monomers having alkylene glycol methacrylate impurities less than 3% and with ethylene glycol dimethacrylate greater than 0.15%. As Table I shows, substantially gel-free hydrophilic poly 2-hydroxyethyl methacrylates can be synthesized in ethanol. The poly 2-hydroxyethyl methacrylates can achieve molecular weights, Mw (weight average molecular weight), from about 176,000 to about 1,000,000, molecular weights, Mn (number average molecular weight), from about 59,000 to about 250,000, solids contents of about 30 weight percent, and a viscosity of about 1000 to about 151,000 cPs.

TABLE I

Synthesis of Poly 2-hydroxyethyl methacrylate in Ethanol

| Example No. | 2 | 3 | 4 | 5 | 6 | C7 | C8 |
| --- | --- | --- | --- | --- | --- | --- | --- |
| HEMA used[a] | Mitsubishi | Mitsubishi | Mitsubishi | Mitsubishi | Mitsubishi | Rohm & Haas | Rohm & Haas |
| Initiator | AIBN[b], 0.5% | BPo[c], 0.5% | BPo, 0.5% | BPo, 0.5% | BPo, 0.25% | AIBN, 0.5% | AIBN, 0.5% |
| Solids Content, % | 30 | 30.9 | 30.5 | 30.7 | 31.3 | gelled | gelled |
| Viscosity, cPs | 1090 | 7100 | 8700 | 15150 | 8200 | — | — |
| Mol. wt, Mw | 176,000 | 420,000 | 483,000 | 874,000 | 1,070,000 | — | — |
| Mol. wt, Mn | 59,200 | 68,000 | 78,700 | 187,000 | 252,000 | — | — |

[a] source of 2-hydroxyethyl methacrylate monomer
[b] AIBN (azobisisobutyronitrile)
[c] BPO (Benzoyl Peroxide)

Molecular weight: 483K, PD 6.1

The appearance of the polymeric product in this example was determined utilizing a visual test looking at the clarity and color of the polymeric product. The presence of any gel in the polymeric product was determined by pouring a thin film of the product and visually inspecting for any particulate.

The percent solids in the polymeric product was measured by accurately weighing a small aluminum dish, then accurately weighing about 1 gram of wet polymer sample. The aluminum dish with the sample was dried under an infrared lamp for about 15 minutes. The aluminum dish with the dried sample was cooled and then accurately reweighed. The weight of the dried sample divided by the wet sample multiplied by 100 is the percent total solids in the sample.

The viscosity of the polymeric product was measured under ambient conditions (23–35° C.) with a Brookfield LV Viscometer using an appropriate spindle and speed for the measured viscosity. The viscosity units are centipoise, cPs.

The molecular weight of the polymeric product was measured using Gel Permeation Chromatography (GPC) in methanol with polyethylene glycol standards.

The protocols described hereinabove that were used to measure and evaluate the appearance, percent solids, viscosity and molecular weight of the polymeric product of Example No. 1 apply to all of the representative homopolymer and copolymer products produced according to the present invention, unless specifically indicated.

Example Nos. 2–6 are representative poly 2-hydroxyethyl methacrylates prepared in ethanol according to the present invention with 2-hydroxyethyl methacrylate monomers having alkylene glycol methacrylate impurities less than 3%, and wherein the alkylene glycol methacrylate impurities comprise ethylene glycol dimethacrylate impurities are between 0.05 and 0.1% by weight, and are compared to Comparative Example Nos. 7 and 8, which are poly Table I shows that the preparation of poly 2-hydroxyethyl methacrylate (poly HEMA) polymers, substantially in the absence of chain transfer agents, using the Mitsubishi HEMA monomer source having acceptable impurity levels provides high molecular weight gel free poly HEMA solution in alcohol. The molecular weight of the polymers can be varied by adjusting the type and amount of initiator used. The use of the AIBN initiator provides the lowest molecular weight polymer. In contrast, the poly HEMA prepared with Rohm & Haas HEMA monomer having 0.17% ethylene glycol dimethacrylate impurity levels, provided a gelled poly HEMA in alcohol, even when using AIBN as the initiator.

EXAMPLE 9

Preparation of poly 2-Hydroxyethyl Methacrylate in Methanol

Recipe (982 Gram Batch)

| Reactor Charge | |
| --- | --- |
| 2-Hydroxyethyl Methacrylate (Mitsubishi) | 300 grams |
| Methanol | 700 grams |
| AIBN (2,2'-azobis(isobutyronitrile) | 1.5 grams |
| Cook-Off initiator | |
| Methanol | 15 grams |
| AIBN (2,2'-azobis(isobutyronitrile) | 0.75 grams |

Procedure

1. The Reactor Charge was weighed out into a flask and poured into a reaction kettle with mixing, and was heated with an 65° C. jacket and a $N_2$ purge kettle.
2. The Cook-Off initiator (Methanol and AIBN) was weighed into a small beaker and mixed until the solids dissolved.

3. Six hours after adding the Reactor Charge the Cook-Off initiator was added.
4. Four hours after adding the Cook Off initiator, the kettle contents were cooled and discharged.

The polymeric product synthesized in Example No. 9, above, exhibited the following properties:
Appearance: clear to light-yellow gel-free liquid
Solids: 36.7%
Viscosity: 39,000 cPs
Residual monomer: HEMA, 0.78%
Molecular weight: Mw=2,260K, PD 4

The shear (min) and 180° peel adhesion properties of pressure sensitive adhesives prepared according to the present invention was evaluated. Table II, below, shows the shear properties and peel adhesion properties of pressure sensitive adhesives on substrates, such as stainless steel, high density polyethylene, and recycled cardboard. As Table II shows, pressure sensitive adhesives prepared by blending poly 2-hydroxyethyl methacrylate synthesized in methanol with 2-hydroxyethyl methacrylate monomers having alkylene glycol methacrylate impurities less than 3% by weight and with ethylene glycol dimethacrylate less than 0.1% and polyethylene glycol (PEG) have a 180° peel adhesion after twenty minutes of about 0.75 lb/in to about 4 lb/in on a stainless steel substrate, a 180° peel adhesion of about 0.2 lb/in to about 0.4 lb/in on a high density polyethylene substrate, and a 180° peel adhesion of about 1 lb/in to about 2 lb/in on a recycled cardboard substrate.

Table II also shows that pressure sensitive adhesives prepared by blending poly 2-hydroxyethyl methacrylate prepared with 2-hydroxyethyl methacrylate monomers having alkylene glycol methacrylate impurities less than 3% by weight and with ethylene glycol dimethacrylate impurity less than 0.1% with polyethylene glycol has a 180° peel adhesion after 24 hours of about 2.3 lb/in to about 4.3 lb/in on a stainless steel substrate, a 180° peel adhesion of about 0.3 lb/in to about 1 lb/in on a high density polyethylene substrate, and a 180° peel adhesion of about 2 lb/in to about 3.7 lb/in on a recycled cardboard substrate.

sensitive adhesive. Preferably, a polyHEMA:PEG ratio of about 1.2:0.8 is used to prepare the pressure sensitive adhesive.

EXAMPLE 13

Preparation of HEMA/Methacrylic Acid Copolymer in Water

Recipe (1200 g Batch)

| | |
|---|---:|
| Reactor Charge | |
| Deionized Water | 400.00 g |
| Initiator Charge | |
| Deionized Water | 100.00 g |
| Sodium Persulfate | 1.5 g |
| Monomer Feed | |
| 2-Hydroxyethyl Methacrylate | 270.0 g |
| Methacrylic Acid | 30.00 g |
| Deionized Water | 300.00 g |
| Ammonium Hydroxide (30%) | 12.3 g |
| Cook-Off Initiator #1 | |
| Deionized Water | 50.0 g |
| Sodium Persulfate | 0.75 g |
| Cook-Off Initiator #2 | |
| Deionized Water | 50.0 g |
| Sodium Persulfate | 0.75 g |

Procedure

1. The Reactor Charge was weighed out into a flask and poured into a reaction kettle.
2. The Reactor Charge was heated with an 80° C. jacket and a $N_2$ purge kettle.
3. The Monomer Feed (2-hydroxyethyl methacrylate, methacrylic acid, deionized water) was weighed into a feed jar, then ammonium hydroxide was added with mixing to adjust the pH to about 5.5.

TABLE II

Poly 2-Hydroxyethyl Methacrylate synthesized in Methanol and Pressure Sensitive Adhesives

| Example No. | Resin/ Peg | Coat Weight g/m² | Shear, min ¼ in², 500 g | 180° Peel, lb/in 20', SS | 180° Peel, lb/in 20', HDPE | 180° Peel, lb/in 20', RC | 180° Peel, lb/in 24 h, SS | 180° Peel, lb/in 24 h, HDPE | 180° Peel, lb/in 24 h, RC |
|---|---|---|---|---|---|---|---|---|---|
| 10 | 1:1 | 38.1 | 2 c | 0.75 p | 0.2 p | 2.0 sl. c | 2.3 p | 0.3 p | 2.6 c |
| 11 | 1.2:0.8 | 33.6 | 98 c | 4.0 pt | 0.4 p | 1.7 sl. pt | 4.2 pt | 1.0 p | 3.7 pt |
| 12 | 1.3:0.7 | 30.7 | 143 c | 3.5 pt | 0.3 p | 1.1 sl. pt | 4.3 pt | 0.6 p | 2.0 pt |

SS - stainless steel; HDPE - high density polyethylene; RC - recycled cardboard c - cohesive; p - panel; pt - paper tear; sl. - slight Table II shows that polyHEMA polymers prepared in alcohol can be formulated with a plasticizer, such as polyethylene glycol (PEG) 400 (Carbowax; Union Carbide) to provide a pressure sensitive adhesive. The adhesive performance of the pressure sensitive adhesive can be varied by adjusting the amount of polyethylene glycol used in the preparation. A polyHEMA:PEG ratio in the range of about 1.5:0.5 to about 0.5:1.5 is used to prepare the pressure 4. The Initiator Charge (sodium persulfate and deionized water) was weighed out into a small beaker and mixed until the solid dissolved.
5. The Initiator Charge was poured into the reaction kettle with the heated and $N_2$-purged Reactor Charge.
6. After 10 minutes, the Monomer Feed was started for a 3-hour period (3.34 g/min), while maintaining an 80° C. jacket temperature.

7. The Cook-Off Initiator #1 (sodium persulfate and deionized water) was weighed into a small beaker and mixed until the solid dissolved.
8. One hour after the end of the Monomer Feed, the Cook-Off Initiator #1 was poured into the reaction kettle.
9. Cook-Off Initiator #2 (sodium persulfate and deionized water) was weighed into a small beaker and mixed until the solid dissolved.
10. One hour after adding Cook-Off #1, Cook-Off #2 was added.
11. One hour after adding Cook-Off #2, the kettle contents were cooled, then discharged into a quart jar.

The copolymer product synthesized in Example No. 13, above, exhibited the following properties:
Appearance: clear, light yellow gel-free liquid.
Solids: 25.9%
Viscosity: 33,000 cPs
pH: 5.5
Residual monomer: HEMA<0.02%, MAA 0.09%
Molecular weight: MW 392K; polydispersity, the Mw/Mn (PD) 1.7

EXAMPLE 14

Preparation of HEMA/4-HBA Copolymer in Alcohol

Recipe (1003.75 g Batch)

| Reactor Charge | |
|---|---|
| 2-Hydroxyethyl Methacrylate (Mitsubishi) | 150 g |
| 4-Hydroxybutyl Acrylate (4-HBA) | 150 g |
| Ethanol | 600 g |
| Benzoyl Peroxide | 1.5 g |
| Cook-Off Initiator #1 | |
| Ethanol | 33.3 g |
| AIBN (2,2'-azobis[isobutyronitrile]) | 0.75 g |
| Cook-Off Initiator #2 | |
| Ethanol | 33.3 g |
| AIBN (2,2'-azobis[isobutyronitrile]) | 0.75 g |
| Cook-Off Initiator #3 | |
| Ethanol | 33.3 g |
| AIBN (2,2'-azobis[isobutyronitrile]) | 0.75 g |

Procedure

1. The Reactor Charge was weighed out into a flask and poured into a reaction kettle with mixing, heated with a 80° C. jacket, and $N_2$ purged.
2. The Cook-Off Initiator #1 (Ethanol and AIBN) was weighed into a small beaker and mixed until the solids dissolved.
3. Three and one-half hours after adding the Reactor Charge, the Cook-Off Initiator #1 was poured into the reaction kettle.
4. Cook-Off Initiator #2 (Ethanol and AIBN) was weighed into a small beaker and mixed until the solids dissolved.
5. One hour after adding Cook-Off #1, Cook-Off #2 was added.
6. Cook-Off Initiator #3 (Ethanol and AIBN) was weighed into a small beaker and mixed until the solids dissolved.
7. One hour after adding Cook-Off #2, Cook-Off #3 was added.
8. One hour after adding Cook-Off #3, the kettle contents were cooled, then discharged into a quart jar.

The copolymer product synthesized in Example No. 14, above, exhibited the following properties:
Appearance: clear, light yellow gel-free liquid.
Solids: 30.5%
Viscosity: 844 cPs
Residual monomer: HEMA<0.01%, 4-HBA 0.22%
Glass Transition Temperature, $T_g$, 9° C.
% Gel in water: 98%
The copolymer is swellable in water up to twice its weight.

Table III, below, shows the static shear and peel adhesion properties of pressure sensitive adhesives prepared by blending copolymers of poly 2-hydroxyethyl methacrylate and methacrylic acid (HEMA/MAA) with a polyalkylene glycol, such as polyethylene glycol (PEG). Example Nos. 13a and 13b are pressure sensitive adhesives prepared from blending HEMA/MAA copolymers and PEG. The HEMA polymers used in Example Nos. 13a and 13b were synthesized in water. Example No. 15 is a pressure sensitive adhesive prepared from blending HEMA/MAA copolymers and PEG. The HEMA/MAA copolymer used in Example No. 15 was synthesized in methanol. The HEMA polymer used in Example No. 16 was synthesized in methanol.

Static shear measures the time required to remove a test sample from a substrate under a specific load. The test applies to the static force to remove an affixed pressure sensitive adhesive from a standard flat surface when the load acts parallel to the surface in a pure shearing action. In static shear testing, the samples were cut into 12×51 mm test strips. The test strips were applied to brightly annealed, highly polished stainless steel test panels having a typical size of about 50×75 mm, making a sample overlay of 12×12 mm with the test panel. The sample portion on the test panel was rolled on using a 2 kg, 5.45 pli 65 shore "A" rubber-faced roller, rolling back and forth one at a rate of 30 cm/min. After a dwell time of at least 15 minutes under standard laboratory testing conditions, the test panels with the test strips were placed at a 2° angle from the vertical, and a load of 500 g was attached to the end of the test strips. The time (in minutes) for the test sample to fail cohesively was measured by a timer.

To measure the peel adhesion, the adhesive was coated at an approximate coat weight of 25 $g/m^2$ (1.0 mil) onto a silicone coated release liner, and then laminated to a 2 mil Mylar™ facestock to form a laminate construction. The resulting laminate was die-cut into 25×204 mm sized test strips. The test strips were then applied to 50×152 mm brightly annealed, highly polishes stainless steel test panels in the lengthwise direction, and rolled down using a 2 kg 5.45 pli 65 shore "A" rubber faced roller. The roller was rolled back and forth once over the test strip at a rate of 30 cm/min. The samples were conditioned for either 15 minutes or 24 hours in a controlled environment testing room maintained at 20° C. and 50% relative humidity. After conditioning, the test strips were peeled away from the test panel in an Instron Universal Tester according to a modified version of the standard tape method Pressure-Sensitive Tape Council, PSTC-1. The force to remove the adhesive test strips from the test panel was measured in lbs/in. Glass panels and high density polyethylene panels were also used to measure peel adhesion.

Possible adhesion failure modes were: "panel failure", wherein the adhesive construction detached from the panel cleanly, without leaving any residue; "panel staining", wherein the adhesive construction detached cleanly, but left a faint stain or "shadow" on the panel' "cohesive failure", wherein the adhesive construction split apart, leaving residue on the test panel and the facestock; "facestock failure", wherein the adhesive completely detached from the facestock, and transferred to the test panel; and "mixed", wherein mixed failure modes were evident.

As Table III shows, pressure sensitive adhesives prepared with the HEMA/MAA copolymers of the present invention, exhibit a static shear of about 16 to about 170 minutes. Pressure sensitive adhesives prepared with the HEMA/MAA copolymers of the present invention exhibit a 180° peel adhesion on a stainless steel substrate of about 1.7 lb/in to about 3.4 lb/in after twenty minutes, and a 180° peel adhesion on a stainless steel substrate of about 2.7 lb/in to about 4 lb/in after 24 hours.

TABLE III

Pressure sensitive adhesives (PSA) prepared with copolymers of 2-hydroxyethylmethacrylate and methacrylic acid

| Example No. | Composition HEMA/MAA | Poly-mer:PEG | Shear, Min ¼ in², 500 g | 180° Peel, SS 20 min. | 24 hours |
|---|---|---|---|---|---|
| 13a* | 90:10 | 1:1 | 169.5 c | 1.78 p | 2.78 pk |
| 13b* | 90:10 | 1:1 | 16.5 c | 3.41 p | 4.07 pt |
| 15** | 90:10 | 1:1 | 2.3 c | 0.88 p | 2.45 p |
| 16** | 100% HEMA | 1:1 | 1.8 c | 0.75 p | 2.26 p |

*HEMA/MMA copolymer synthesized in water
**HEMA/MMA copolymer synthesized in methanol
***poly HEMA synthesized in methanol
Mode of failure
c = cohesive
p = panel
pk = fiber pick
pt = paper tear As Table III shows, poly HEMA/methacrylic acid copolymer prepared in water can also be formulated with a plasticizer, such as polyethylene glycol (PEG), to provide pressure sensitive adhesives. The adhesive performance of the pressure sensitive adhesives can be varied by adjusting the amount of PEG added. The results in Table III also show that the adhesive performance of the pressure sensitive adhesives comprising the poly HEMA/methacrylic acid copolymer prepared in water is comparable to the adhesive performance of pressure sensitive adhesives comprising poly HEMA prepared in alcohol, but without the need for the alcohol solvent.

As described hereinabove, the copolymer of 2-hydroxyethyl methacrylate and methacrylic acid prepared in water is also useful as abrasion resistant coatings for glass bottles. Tables IV and V, below, show the results of testing performed on glass beer bottles that were coated with the abrasion resistant coating comprising a copolymer of 2-hydroxyethyl methacrylate and methacrylic acid prepared in water according to the method of the present invention.

TABLE IV

Abrasion Resistant Coating comprising copolymer of poly HEMA/MMA (90/10)

| Example | Crosslinker[a] | Surfactant[b] | Wax[c] | Coating Clarity | Scratch Resistance | Water Resistance | Alkali Removal |
|---|---|---|---|---|---|---|---|
| 17 | 2.5% | 0 | 0 | 5 | 4 | 1 | 4 |
| 18 | 7.5% | 0 | 0 | 5 | 5 | 3 | 3 |
| 19 | 2.5% | 2% | 0 | 5 | 4 | 4 | 2.5 |
| 20 | 2.5% | 0 | 5% | 1 | 5 | 4 | 5 |
| 21 | 7.5% | 0 | 5% | 0 | 5 | 5 | 3 |
| 22 | 5% | 0 | 2.5% | 0 | 5 | 4 | 5 |
| 23 | 5% | 1% | 0 | 5 | 4 | 4 | 5 |

Rating:
0 = worst; 5 = best
a = ammonium dichromate
b = Dow Corning 193 silicone surfactant
c = Michem 68725 wax

TABLE V

Abrasion Resistant Coating comprising copolymer of polyHEMA/MMA (90/10)

| | Example No. 24 | | | Example No. 25 | | |
|---|---|---|---|---|---|---|
| Test | Initial | 1 week, 70° C. | 3 week, 70° C. | Initial | 1 week, 70° C. | 3 week, 70° C. |
| Auto Scratch | Good | Good | Good | OK | OK | OK |
| Scratch Resistance | 5H–6H | 6H | 6H | 5H | 6H | 6H |
| Water Resistance | | | | | | |
| Initial | OK | OK | OK | OK | OK | OK |
| 1 hour | 3H | H | H | 3H | 3H | 3H |
| Caustic Wash | Good | Good | Good | Good | Good | Good |

The auto scratch test is performed by contacting two coated bottles together to facilitate the scratching of the exterior surface of the bottles. The scratch resistance of the coated bottle is measured by using a H to 6H pencil to scratch the exterior surface of the coated bottle. The water resistance of the coated bottle is measured by soaking the coated bottles on deionized water for 48 hours at room temperature. The exterior surface of the soaked bottles are then scratched with an individual's fingernail immediately when taken from the water, or scratched with a H to 6H pencil after one hour of drying at room temperature. The caustic wash test measures the removability of the copolymer coating by alkali treatment. The copolymer coated bottles are placed into a caustic solution, such as 1% sodium hydroxide for 15 minutes at room temperature with magnetic stir bar agitation, followed by rinsing with water.

As Tables IV and V show, that the copolymers of 2-hydroxyethyl methacrylate and methacrylic acid are useful as abrasion resistant coatings for glass bottles. The copolymer coatings prevent scratching of the exterior surface of glass beer bottles, even after soaking in deionized water. In addition, the copolymer coating is easily removed from the exterior surface of the glass bottles by treatment with an alkali solution.

EXAMPLE 26

Preparation of Clear Core/Shell Polymer Emulsion

|  | grams |
|---|---|
| Reactor Charge | |
| Deionized Water | 175.7 |
| Airvol 523 (15% solution) | 65.0 |
| Disponyl FES 77 (32%) | 14.3 |
| NaFeEDTA | 0.02 |
| Tert-Butyl Hydroperoxide | 0.3 |
| Activator Feed | |
| Deionized Water | 150.9 |
| Sodium Formaldehyde Sulfoxylate | 1.1 |
| Core Feeds | |
| Water Soluble Monomer Feed | |
| Deionized Water | 338.0 |
| 2-Hydroxyethyl Methacrylate | 160.0 |
| n-Vinyl Pyrrolidone | 100.0 |
| tert-Butyl Hydroperoxide | 2.0 |
| PreEmulsion Feed | |
| Deionized Water | 105.2 |
| Airvol 523 (15% solution) | 32.5 |
| Disponyl FES 77 (32%) | 14.3 |
| Butyl Acrylate | 100.0 |
| Diethylaminoethyl Methacrylate | 40.0 |
| Shell Feed | |
| 2-Hydroxyethyl Methacrylate | 50.0 |
| n-Vinyl Pyrrolidone | 31.3 |
| Butyl Acrylate | 40.0 |
| Methacrylic Acid | 3.8 |
| Tert-Butyl Hydroperoxide | 0.1 |
| Ammonium Hydroxide (28%) | 1.9 |
| Cook Off | |
| Tert-Butyl Hydroperoxide | 0.5 |
| Total | 1426.8 |

Procedure

1. Heated Reactor Charge to 53–55° C. with a 55° C. jacket. Mixed at 125 RPM and used a nitrogen purge.
2. Added 15 g of PreEmulsion Feed to Reactor.
3. Waited 5 minutes, then added 7 g of Activator solution.
4. Waited 5 minutes, then began 3 Feeds:
   Monomer: 600 g/180 min. (=3.33 g/min)
   PreEmulsion: 277 g/180 min. (=1.54 g/min)
   Activator: 145 ml/270 min. (=0.54 ml/min)
5. 20 minutes after Monomer & PreEmulsion feeds ended, began shell feed: 127 g/60 (=2.1 g/min).
6. Continued Activator feed for 30 minutes after Shell feed ended. Then stopped Activator Feed and added Cook Off.
7. Cooked for 30 minutes, then cool and discharged.

The resulting polymer had the following properties:
   Solids 32.5%
   Viscosity 111 cPs

EXAMPLE 27

Preparation of Clear Core/Shell Polymer Emulsion

|  | grams |
|---|---|
| Reactor Charge | |
| Deionized Water | 143.0 |
| Airvol 523 (10% solution) | 95.7 |
| Disponyl FES 77 (32%) | 14.3 |
| NaFeEDTA | 0.02 |
| tert-Butyl Hydroperoxide | 0.3 |
| Activator Feed | |
| Deionized Water | 135.9 |
| Sodium Formaldehyde Sulfoxylate | 1.1 |
| Core Feeds | |
| Monomer Feed | |
| Deionized Water | 83.0 |
| 2-Hydroxyethyl Methacrylate | 80.0 |
| n-Vinyl Pyrrolidone | 30.0 |
| tert-Butyl Hydroperoxide | 2.0 |
| PreEmulsion Feed | |
| Deionized Water | 36.9 |
| Airvol 523 (10% solution) | 48.8 |
| Disponyl FES 77 (32%) | 14.3 |
| Butyl Acrylate | 63.5 |
| Methyl Acrylate | 9.5 |
| Methyl Methacrylate | 9.5 |
| Diethylaminoethyl Methacrylate | 25.0 |
| Trifluoroethyl Methacrylate | 2.5 |
| Shell Feed-Monomer | |
| 2-Hydroxyethyl Methacrylate | 36.3 |
| n-vinyl Pyrrolidone | 9.9 |
| Dimethylaminoethyl Acrylate-Methyl Chloride Quaternary | 7.1 |
| Methacrylic Acid | 9.9 |
| Methyl Acrylate | 11.0 |
| Methyl Methacrylate | 33.3 |
| Trifluoroethyl Methacrylate | 2.5 |
| tert-Butyl Hydroperoxide | 0.2 |
| Shell Feed-Ammonia | |
| Deionized Water | 107.1 |
| Ammonium Hydroxide (30%) | 5.0 |
| Cook Off | |
| Tert-Butyl Hydroperoxide | 0.5 |
| Total | 1018.1 |

Procedure

1. Heated Reactor Charge to 53–55° C. with a 55° C. jacket. Mixed at 125 RPM and used a nitrogen purge.
2. Added 15 g of PreEmulsion Feed to Reactor.
3. Waited 5 minutes, then added 7 g of Activator solution.
4. Waited 5 minutes, then began 3 Feeds:
   Monomer: 195 g/100 min. (=1.95 g/min)
   PreEmulsion: 195 g/100 min. (=1.95 g/min)
   Activator: 130 ml/240 min. (=0.54 ml/min)
5. 20 minutes after Monomer and PreEmulsion feeds ended, began Shell Monomer feed: 110 g/60 min (=1.83 g/min) and began Shell Ammonia feed: 110 g/60 min (=1.83 g/min).
6. Continued Activator feed for 30 minutes after Shell feed ended. Then stopped Activator Feed and added Cook Off.
7. Cooked for 30 minutes, then cooled and discharged.
   The resulting polymer had the following properties:
   Solids 33.9%

Viscosity 300 cPs

EXAMPLE 28

Preparation of Copolymer by Alkyl Acrylate Emulsion/Water-Soluble Feeds Method

| Reactor Charge | |
| --- | --- |
| Deionized Water | 175.7 g |
| Airvol 523 (15% solution) | 65 g |
| Disponyl FES 77 (32%) | 14.3 g |
| NaFeEDTA | 0.02 g |
| tert-Butyl Hydroperoxide | 0.3 g |
| Monomer Feed | |
| Deionized Water | 338 g |
| 2-Hydroxyethyl Methacrylate | 160 g |
| n-Vinyl Pyrrolidone | 100 g |
| tert-Butyl Hydroperoxide | 2 g |
| PreEmulsion Feed | |
| Deionized Water | 105.2 g |
| Airvol 523 (15% solution) | 32.5 g |
| Disponyl FES 77 (32%) | 14.3 g |
| Butyl Acrylate | 100 g |
| Diethylaminoethyl Methacrylate | 40 g |
| Activator Feed | |
| Deioinized Water | 135.9 g |
| Sodium Formaldehyde Sulfoxylate | 1.1 g |
| Cook Off | |
| tert-Butyl Hydroperoxide | 0.5 g |
| Total | 1284.8 g |

Procedure

1. The reactor charge was heated to about 53–55° C. with a 55° C. jacket. Mixed at 125 RPM and used a nitrogen purge.
2. 15 g of PreEmulsion Feed was added to the reactor.
3. After 5 minutes, 7 g of Activator solution was added to the reactor.
4. After 5 minutes, begin to add three feeds:
   Monomer Feed 600 g/210 minutes (2.86 g/min)
   PreEmulsion Feed 277 g/210 minutes (1.32 g/min)
   Activator Feed 130 ml/240 minutes (0.54 ml/min)
5. Continue to add Activator Feed for 30 minutes after Monomer and PreEmulsion feeds end.
6. Stop adding Activator Feed and add Cook Off.
7. Cook for 30 minutes, then cool and discharge.

The resulting polymer had the following properties:

| Solids | 31.8% |
| --- | --- |
| Viscosity | 78 cPs |

Example No. 28 is a poly 2-hydroxyethylmethacrylate copolymer prepared in water emulsions according to the Alkyl Acrylate emulsion/water-soluble feeds method of the present invention. Example Nos. 29–31 are poly 2-hydroxyethylmethacrylate copolymers prepared in water emulsions according to the core/shell method of the present invention. Example Nos. 28–31 were evaluated as coatings for ink jet applications. Example No. 29 of Table VI is the copolymer prepared according to Example No 26 described hereinabove. Example No. 31 of Table VI is the copolymer prepared according to Example No. 27 described hereinabove. The copolymer coatings of the present invention were compared to Comparative Example Nos. 32–35.

The poly 2-hydroxyethyl methacrylate copolymer emulsions of Example Nos. 28–31 were coated onto Mylar™ clear polyester films (Dupont; Wilmington, Del.) having a thickness of 4 millimeters (mm) at a coat weight of about 20 to about 25 g/m². The coating was dried at 70° C. for about 15 minutes. The clear polyester film having the dried coating thereon was cut into 8½"×11" sheets for testing.

Comparative Example Nos. 32 and 33 are premium inkjet transparency films for overhead projectors that are commercially available from Hewlett Packard Company (Palo Alto, Calif.) and Minnesota Mining and Manufacturing Company (3M; Saint Paul, Minn.). Comparative Example No. 34 is a premium glossy paper for inkjet printer that comprises a clear polyester film with an opaque coating thereon that is commercially available from Hewlett Packard Company. Comparative Example No. 35 is a plain clear polyester film without a coating.

The poly 2-hydroxyethyl methacrylate copolymer coatings were evaluated for clarity, image quality, drying time, ink density, and water resistance. Each property was evaluated on a scale from 1 to 5, with 1 being the lowest possible rating and 5 being the highest possible rating.

The clarity was evaluated by a visual inspection of the coated film before printing for haziness and particulate matter.

The image quality was evaluated by a visual inspection performed after printing. The visual inspection was performed using a 10× magnifying glass, looking for indications of "feathering", which represents fuzzy edges of images, "mud cracking", and "cascading", which is a measure of the coverage in the fill areas.

The ink density was measured after printing using a densitometer (Tobias IQ 150 portable reflection densitometer) in a 100% fill area of each color. The units for ink density are density units.

The drying time of the ink on the coated films was measured immediately after the printing was completed. The dry time was tested by testing the smearing of the various colors on the film every 30 seconds until the ink dried. The time indicated in Table VI is the time for the last color to smear. Although the testing was performed on film, it is important to note that the acrylic emulsion ink jet receptive coatings of the present invention are also useful as glossy coatings on paper that is to be utilized for ink jet printing.

The water resistance was tested about 20 minutes after the printing was completed. Each example was held at an angle while about 5 ml of water was dripped onto the 100% fill area of each color. The results of the above described tests are set forth in Table VI, below.

TABLE VI

Evaluation of 2-hydroxyethyl methacrylate copolymers as ink jet coatings

| Example No. | 28 | 29 | 30 | 31 | C32 | C33 | C34 | C35 |
|---|---|---|---|---|---|---|---|---|
| Coat Weight | 25 | 19 | 22 | 21 | — | — | — | — |
| Clarity* | 4 | 4 | 4.5 | 3 | 1 | 2 | opaque | 5 |
| Image Quality* | 3 | 3 | 3.5 | 3.5 | 3 | 3 | 4 | 1 |
| Ink Density | | | | | | | | |
| Black | 0.82 | 0.88 | 1.42 | 1.42 | 1.82 | 2.04 | 1.76 | 0.34 |
| Cyan | 0.74 | 0.76 | 0.87 | 0.85 | 0.70 | 0.72 | 0.71 | 0.96 |
| Magenta | 1.74 | 1.82 | 1.88 | 1.82 | 1.45 | 1.59 | 1.33 | 1.17 |
| Yellow | 1.2 | 1.19 | 1.25 | 1.25 | 1.25 | 1.19 | 1.29 | 0.21 |
| Drying Time, minutes | 3 | 3 | 2 | 2 | 1.5 | 1.5 | 1 | 1200 |
| Water Resistance* | 2 | 2.5 | 4 | 4 | 2 | 1 | 3 | 1 |

*1 (worst)–5 (best)

Comparative Example Nos. C32 and C33 are commercially available ink jet transparency films having a grainy appearance. Comparative Example No. C34 is a commercially available ink jet paper that is a pigmented film. Comparative Example No. C35 is a commercially available plain polyester film without a coating, which does not absorb or dry ink. As one can see from Table VI, the hydrophilic emulsions of the present invention are particularly useful as clear coatings for ink jet recording films. The clear coatings provide excellent performance without the need for the addition of pigments and, therefore, avoids the grainy/hazy appearance associated with the commercially available films.

EXAMPLE 36

Preparation of poly(HEMA) Powder

Recipe (100 Gram Batch)
The following were added to a reaction vessel with stirring:

| Deionized Water | 60.0 g |
|---|---|
| 2-Hydroxyethyl Methacrylate (Mitsubishi) | 30.0 g |

After 15 minutes of a nitrogen purge, the following was added:
  Sodium Metabisulfite (10% solution) 5.0 g
After an additional 15 minutes of a nitrogen purge, the following was added:
  Sodium Metabisulfite (10% solution) 5.0 g
The reaction was held at ambient temperature for an additional 4 hours with a constant nitrogen flow. The product was chopped and leached overnight, then dried. The dried product was ground up into a powder (about 50 microns). The product synthesized in Example No. 36, above, exhibited 9.7%, gel as determined by the gel content method described hereinabove.

The powder (25 g) was compounded with PEG 400 polyethylene glycol (25 g) to form a pressure-sensitive adhesive. PEG 400 polyethylene glycol is commercially available from Union Carbide under the trade designation Carbowax®, Sentry Grade, Polyethylene Glycol 400.

The tack of the pressure sensitive adhesive was determined by a modified spherical probe adhesion test that involves recording and analyzing the entire stress-strain behavior of a pressure sensitive adhesive during bonding and debonding of the probe. The test apparatus consists of a stainless steel spherical probe connected to a force transducer. The force transducer measures the force acting upon the spherical probe. The probe is moved up and down by a rotating screw driven by a stepping motor. A pressure sensitive adhesive sample is bonded adhesive side up to the test platform with a double-sided tape. During bonding of the probe to the pressure sensitive adhesive, the probe moves down and compresses the adhesive to a predetermined force (i.e.—compression force). During the debonding process, the probe ascends and separates from the pressure sensitive adhesive sample and a predetermined test speed. As the probe ascends, the adhesive sample becomes elongated and exerts a tensile force on the transducer. As the adhesive is further elongated, the stress increases in the adhesive until it reaches the interfacial strength between the probe and the adhesive, at which point the probe separates from the adhesive sample. The debonding strength of the adhesive sample is measured by the magnitude of the force and duration time of the probe. The pressure sensitive adhesive of Example No. 36 exhibited a tack value of 0.2303 N Force and 93.965 Nm ($\times 10^{-5}$) Energy. For a detailed description for the measurement of the tack of pressure sensitive adhesives, see "Avery Adhesive Test, AAT", *Adhesives Age*, Vol. 10, No. 10, pp.18–23 (1997).

Example Nos. 37–45 are examples of 1–1.5 mm thick pressure sensitive adhesives comprising poly 2-hydroxyethyl methacrylate powders blended with polyethylene glycol (PEG) 400 at a powder:PEG ratio of 1:2. The poly 2-hydroxyethyl methacrylate powders were prepared using different HEMA monomer sources. The tack and rheometrics of the pressure sensitive adhesives are reported in Table VIIa, below.

TABLE VIIa

Pressure Sensitive Adhesives of
poly 2-hydroxyethyl methacrylate and polyethylene glycol

| | | | | | Rheometrics | | | |
|---|---|---|---|---|---|---|---|---|
| Ex. | % INT/ACT | % Gel | Force (N) | Energy Nm ($10^{-5}$) | G' 0.1 rad/s dyne/ cm × $10^4$ | G' 100 rad/s dyne/ cm × $10^4$ | G" 0.1 rad/s dyne/ cm × $10^4$ | G" 100 rad/s dyne/ cm × $10^4$ |
| 37* | 0.1 | 98.5 | 0.1312 | 3.4189 | 17.8420 | 2.0629 | 33.9930 | 6.7337 |
| 38* | 0.8 | 85.8 | 0.1827 | 15.0930 | 4.3926 | 0.7101 | 13.9110 | 5.0524 |
| 39* | 1.6 | 76.5 | 0.1535 | 17.6360 | 1.8554 | 0.3791 | 8.6069 | 4.4009 |
| 40** | 0.1 | 97.1 | 0.2215 | 6.2883 | 17.2500 | 2.6183 | 31.8970 | 5.3206 |
| 41** | 0.8 | 63.8 | 0.1332 | 67.8080 | 0.8932 | 0.6411 | 10.5470 | 5.0334 |
| 42** | 1.6 | 14.8 | 0.0531 | 153.7300 | 0.0817 | 0.1560 | 6.3956 | 4.6835 |
| 43*** | 0.1 | 96.7 | 0.1476 | 4.4343 | 2.8014 | 0.3687 | 5.4282 | 1.0169 |
| 44*** | 0.8 | 73.5 | 0.1757 | 33.4000 | 3.2641 | 1.0506 | 18.8390 | 8.1289 |
| 45*** | 1.6 | 59.2 | 0.0500 | 22.6810 | 0.2321 | 0.1943 | 6.6193 | 5.1477 |

HEMA sources:
*Rohm & Haas OGM,
**Mitsubishi SEC,
***RohmTech BM 903

Table VIIA shows poly HEMA powder prepared with various sources of HEMA monomers, and various ratios of initiator/activator can be formulated with polyethylene glycol to form a pressure sensitive adhesive. The pressure sensitive adhesives have good adhesive performance (i.e.— high Force and Energy as measured by the ATT test described hereinabove).

Example No. 46-54 in Table VIIb are examples of pressure sensitive adhesives comprising poly 2-hydroxyethyl methacrylate powders blended with polyethylene glycon (PEG) 400 at powder:PEG ratios of 1:1, 1:2 and 1:3. The poly 2-hydroxyethyl methacrylate powders were prepared with HEMA monomers commercially available from Mitsubishi. The tack, including Force (N) and Energy (Nm× $10^{-5}$) of the pressure sensitive adhesives are reported in Table VIIb, below.

TABLE VIIb

Pressure Sensitive Adhesives of
poly 2-hydroxyethyl methacrylate* and polyethylene glycol

| Example* | % INT/ACT | % Gel | Powder:PEG | Force (N) | Energy Nm(×$10^{-5}$) |
|---|---|---|---|---|---|
| 46 | 0.1 | 95.7 | 1:1 | 0.1504 | 2.8897 |
| 47 | 0.8 | 66.2 | 1:1 | 0.2626 | 14.8660 |
| 48 | 1.6 | 9.7 | 1:1 | 0.2303 | 93.9650 |
| 49 | 0.1 | 97.1 | 1:2 | 0.2215 | 6.2883 |
| 50 | 0.8 | 63.8 | 1:2 | 0.1332 | 67.8080 |
| 51 | 1.6 | 14.8 | 1:2 | 0.0531 | 153.7300 |
| 52 | 0.1 | 95.7 | 1:3 | 0.1184 | 4.1229 |
| 53 | 0.8 | 66.2 | 1:3 | 0.0450 | 21.1301 |
| 54 | 1.6 | 9.7 | 1:3 | elongation too high | |

*Mitsubishi SEC

Table VIIb shows that low gel polyHEMA powder prepared with the Mitsubishi HEMA monomers formulated with lower levels polyethylene glycol provides the highest ATT values. Because of the low gel content of the polyHEMA powder, it is possible to reduce the amount of plasticizer used to prepare a pressure sensitive adhesive.

Example Nos. 55–61 in Table VIII are poly 2-hydroxyethyl methacrylate polymers prepared by blending 2-hydroxyethyl methacrylate monomers having less than 3 weight percent alkylene glycol methacrylate impurities and containing 0.05–0.1% by weight of ethylene glycol dimethacrylate with 2-hydroxyethyl methacrylate monomers having less than 3 weight percent alkylene glycol methacrylate impurities and greater than 0.15% by weight of ethylene glycol dimethacrylate. The poly HEMA powders were formulated with PEG at a ratio of one part poly HEMA powder to two parts PEG plasticizer. As shown in Table VIII, poly 2-hydroxyethyl methacrylate prepared according to the present invention having a %INT/ACT from about 0.1 to about 1.6 exhibit a Force of about 0.12 N to about 0.2 N and an Energy of about 4.7 Nm (×$10^{-5}$) to about 40 Nm (×$10^{-5}$).

The rheometrics for the poly 2-hydroxyethyl methacrylate was also evaluated. A detailed description relating to the measurement of modulus is provided in "Viscoelastic Windows of Pressure-Sensitive Adhesives", E. P. Chang, J. Adhesion, Vol. 34 pp. 189–200 (1991), and "Viscoelastic Properties of Pressure-Sensitive Adhesives", E. P. Chang, J. Adhesion, Vol. 60 pp. 233–248, (1997). Briefly, dynamic shear modulus (G) can be resolved into components of storage modulus (G') plus dissipation modulus (G"). In dynamic mechanical testing with varying amplitude and frequency, sinusoidal deformation is applied to the test sample and the resultant torque or force transmitted through the sample to a transducer is measured. Both the strain and the torque signals are amplified and input to a central processing unit where the phase angle between the strain and torque and the dynamic modulus are calculated using programs related to the test mode and sample geometry selected.

TABLE VIII

| | | | | | Avery Tack | | | | |
|---|---|---|---|---|---|---|---|---|---|
| | | | | | Energy | Rheometrics dyne/cm × $10^4$ | | | |
| Ex. | HEMA OGM*:SEC** | % INT/ACT | % Gel | Force (N) | Nm ($10^{-5}$) | G' 0.1 rad/s | G' 100 rad/s | G" 0.1 rad/s | G" 100 rad/s |
| 55 | 50:50 | 0.1 | 93.3 | 0.1391 | 4.719 | 17.0220 | 30.8500 | 2.2762 | 5.1992 |
| 56 | 50:50 | 0.8 | 75.8 | 0.1999 | 26.223 | 2.8982 | 12.8910 | 0.8750 | 4.8199 |
| 57 | 50:50 | 1.6 | 58.9 | 0.1290 | 39.340 | 0.5618 | 5.5776 | 0.2443 | 3.1655 |
| 58 | 75:25 | 0.1 | 92.0 | 0.1464 | 4.998 | 6.5796 | 13.2500 | 0.9310 | 2.6070 |
| 59 | 75:25 | 0.8 | 79.7 | 0.1560 | 14.257 | 5.2057 | 17.9140 | 1.1070 | 5.9671 |
| 60 | 75:25 | 0.8 | 78.8 | 0.1675 | 15.706 | 5.8394 | 20.0840 | 1.2593 | 6.8274 |
| 61 | 75:25 | 1.6 | 62.2 | 0.1647 | 24.573 | 1.4052 | 9.5499 | 0.4508 | 5.0231 |

*Mitsubishi SEC
**Rohm & Haas Rocryl OGM

Table VIII shows that pressure sensitive adhesives having adequate ATT performance can be prepared using a combination of low gel producing HEMA monomers (Mitsubishi) and high gel producing HEMA monomers (Rohm & Haas).

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A method of preparing a substantially gel free, hydrophilic, water soluble polymer substantially in the absence of a chain transfer agent, said polymer comprising a copolymer of 2-hydroxyethyl methacrylate and acrylic acid or methacrylic acid including:

introducing monomeric 2-hydroxyethyl methacrylate containing at least 0.05% by weight of ethylene glycol dimethacrylate and at least one of acrylic acid and methacrylic acid into water solution, adjusting the pH of the solution to a pH in the range of greater than about pH 3 to less than about pH 9, and copolymerizing the monomeric 2-hydroxyethyl methacrylate and acrylic acid or methacrylic acid to form a polymerization mixture.

2. The method of claim 1, further including removing the water from the polymerization mixture after said copolymerizing.

3. The method of claim 1, wherein said one of acrylic acid or methacrylic acid is introduced into the water solution in a weight ratio in the range of about 3 to about 15%.

4. A method of preparing a hydrophilic pressure sensitive adhesive comprising:

(a) preparing a substantially gel free, hydrophilic, water soluble polymer, said polymer comprising a copolymer of 2-hydroxyethyl methacrylate and acrylic acid or methacrylic acid including (i) introducing monomeric 2-hydroxyethyl methacrylate and at least one of acrylic acid and methacrylic acid into water solution, (ii) adjusting the pH of the solution to a pH in the range of greater than about pH 3 to less than about pH 9 and (iii) copolymerizing the monomeric 2-hydroxyethyl methacrylate and acrylic acid or methacrylic acid to form a polymerization mixture, (b) adding a polyalkylene glycol to the polymerization mixture and (c) removing the water to form a hydrophilic pressure sensitive adhesive.

5. The method of claim 4, wherein the polyalkylene glycol is selected from the group consisting polyethylene glycol, polypropylene glycol and copolymers of ethylene glycol and propylene glycol, and mixtures thereof.

6. A method of coating a substrate comprising applying to said substrate, the pressure sensitive adhesive as prepared in claim 4.

7. The method of claim 6 wherein the substrate is a release liner.

8. A substrate coated in accordance with the method of claim 6.

9. A release liner coated in accordance with the method of claim 6.

10. A method of preparing a flexible hydrophilic coating comprising:

(a) preparing a substantially gel free, hydrophilic, water soluble polymer, said polymer comprising a copolymer of 2-hydroxyethyl methacrylate and acrylic acid or methacrylic acid including (i) introducing monomeric 2-hydroxyethyl methacrylate and at least one of acrylic acid and methacrylic acid into water solution, (ii) adjusting the pH of the solution to a pH in the range of greater than about pH 3 to less than about pH 9 and (iii) copolymerizing the monomeric 2-hydroxyethyl methacrylate and acrylic acid or methacrylic acid to form a polymerization mixture, (b) adding glycerin to the polymerization mixture and (c) removing the water by drying to form a flexible hydrophilic coating.

11. A method of coating a substrate comprising applying to said substrate the hydrophilic polymer as prepared in claim 10.

12. A substrate coated in accordance with the method of claim 11.

13. A polymeric film coated in accordance with the method of claim 11.

14. The method of claim 11 wherein the substrate is a polymeric film.

15. The method of claim 14 wherein the polymeric film is formed from a thermoplastic material.

* * * * *